United States Patent [19]
Clauson et al.

[11] Patent Number: 5,423,327
[45] Date of Patent: Jun. 13, 1995

[54] METHOD FOR AUTOMATIC STIMULATION OF MAMMELS IN RESPONSE TO BLOOD GAS ANALYSIS

[76] Inventors: William L. Clauson, 74 Manzanita Rd., Atherton, Calif. 94027; Nir A. Imran, 731 Barron Dr., Palo Alto, Calif. 94306

[21] Appl. No.: 232,603

[22] Filed: Apr. 25, 1994

Related U.S. Application Data

[60] Division of Ser. No. 799,557, Nov. 27, 1991, Pat. No. 5,329,931, which is a continuation-in-part of Ser. No. 313,592, Feb. 21, 1989, abandoned.

[51] Int. Cl.[6] .............................................. A61B 5/08
[52] U.S. Cl. ..................... 128/716; 128/633; 128/634; 128/665; 607/75; 607/42; 607/62
[58] Field of Search ............. 128/633, 634, 664–666, 128/716, 721, 420–420.5, 421, 422, 632; 607/75, 145, 42, 62

[56] References Cited

U.S. PATENT DOCUMENTS

| | | | |
|---|---|---|---|
| 3,802,417 | 4/1974 | Lang | 128/716 |
| 4,813,427 | 3/1989 | Schlaefke et al. | 128/716 |
| 4,827,935 | 5/1989 | Geddes et al. | 128/123 |
| 5,273,036 | 12/1993 | Kronberg et al. | 128/716 |
| 5,277,193 | 1/1994 | Takishima et al. | 128/716 |

*Primary Examiner*—Lee S. Cohen
*Assistant Examiner*—Brian L. Casler
*Attorney, Agent, or Firm*—Flehr, Hohbach, Test, Albritton & Herbert

[57] ABSTRACT

Method for automatic stimulation of a patient comprising sensing the saturation level or absolute or actual value of a predetermined gas in the blood of the patient and supplying an electrical signal representative of that measured saturation level, generating a control signal in response to the electrical signal when the measured saturation level falls below the predetermined value and automatically stimulating the patient when a control signal is received.

4 Claims, 3 Drawing Sheets

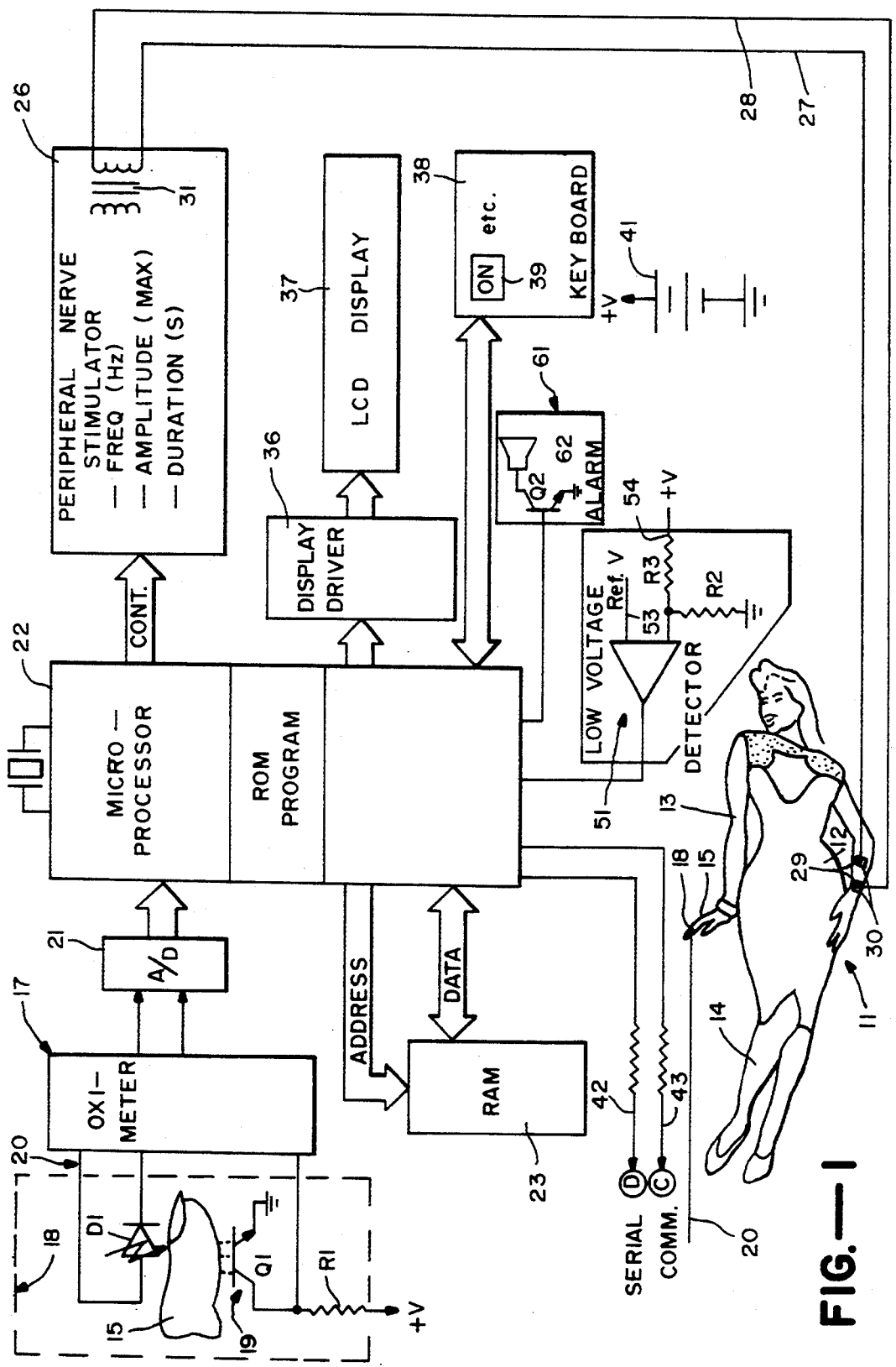
FIG.—1

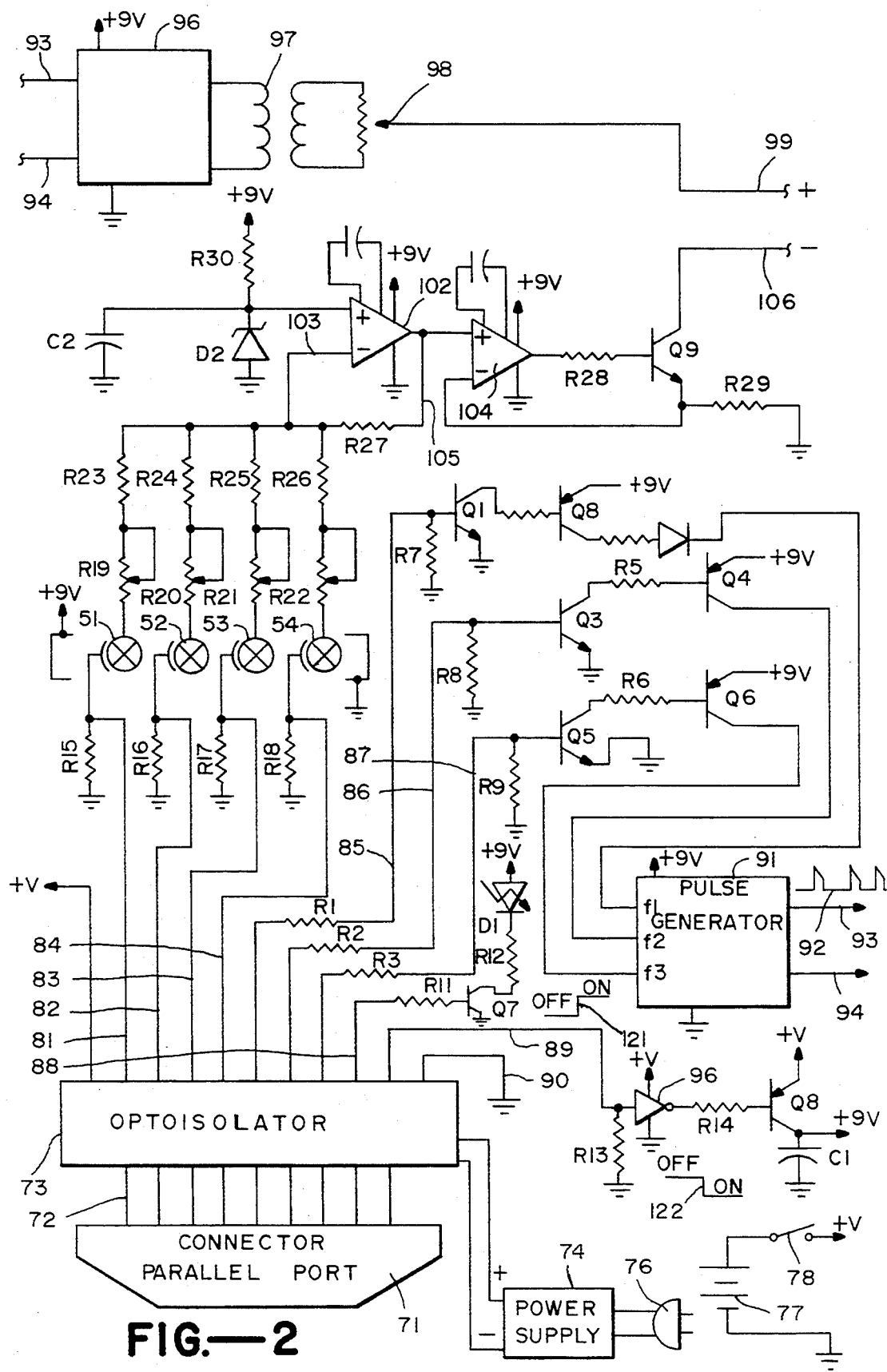
FIG.—2

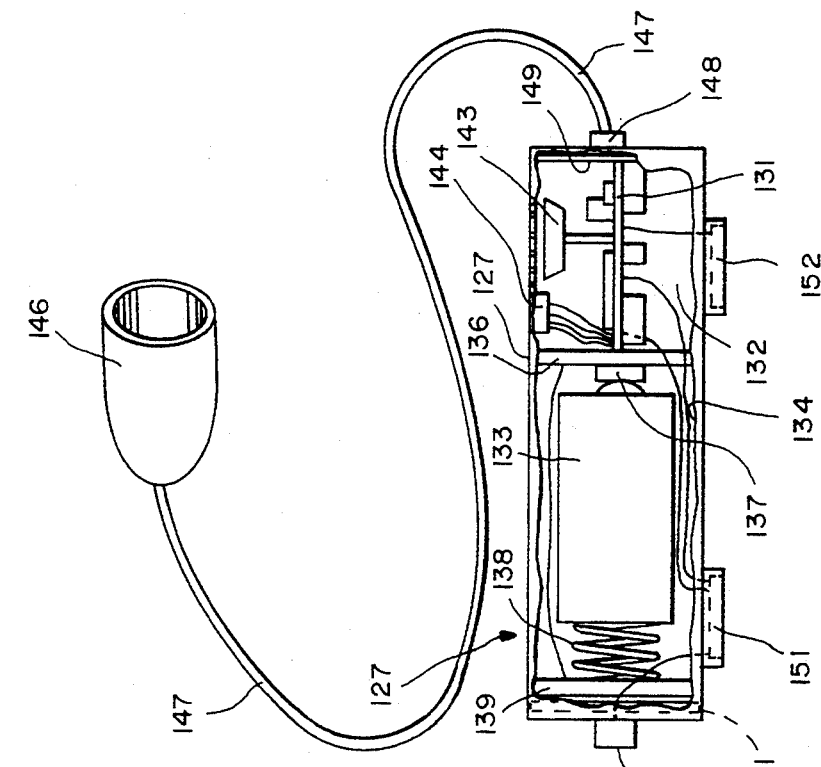
FIG.—4
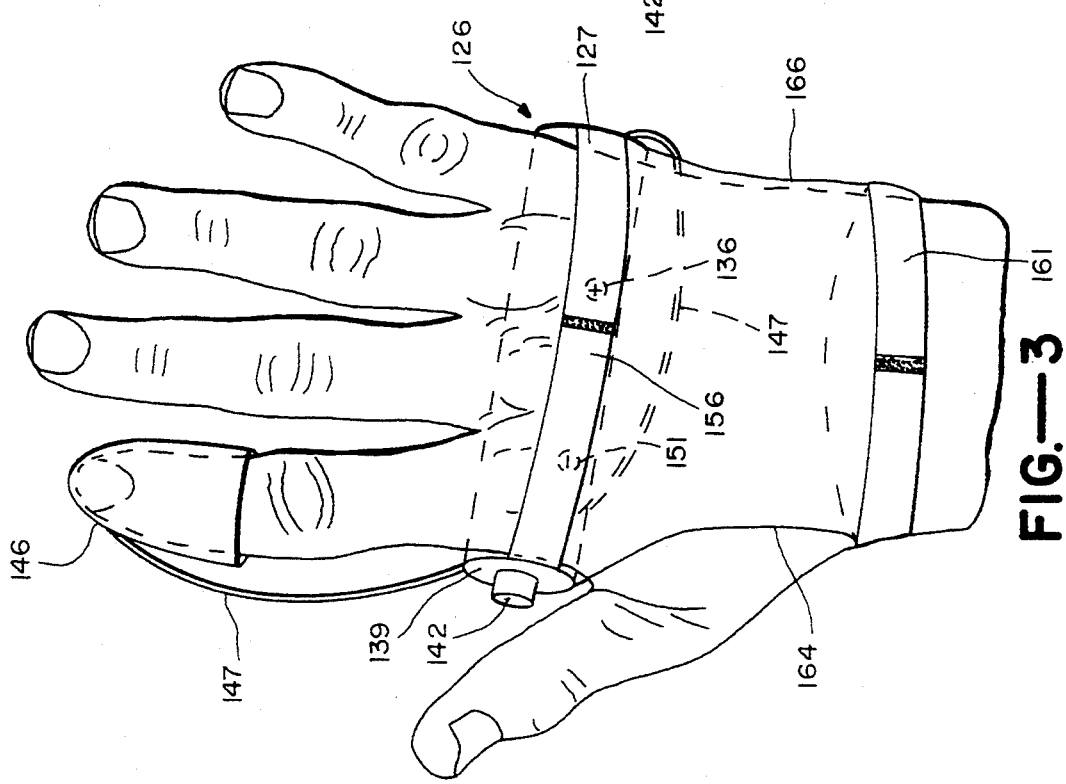
FIG.—3

METHOD FOR AUTOMATIC STIMULATION OF MAMMELS IN RESPONSE TO BLOOD GAS ANALYSIS

This is a division of application Ser. No. 07/799,557, filed Nov. 27, 1991 U.S. Pat. No. 5,329,981, which is a continuation in part of application Ser. No. 07/313,592 filed on Feb. 21, 1989, now abandoned.

This invention relates to an apparatus and method for automatic stimulation of breathing mammals in response to blood gas analysis and more in particular to detection of apnea conditions.

At the present time, transcutaneous, membranous instruments are available for measuring a patient's oxygen and carbon dioxide status non-invasively and continuously by measuring the oxygen and the carbon dioxide concentration in the skin tissue of the patient. Also peripheral nerve stimulators are available. Also available are pulse oximeters to reliably measure hemoglobin saturation within oxygen by finger or earlobe sensors. In addition, external tidal capnographs are readily available to measure exhaled lung carbon dioxide as an indirect but accurate reflection of blood carbon dioxide. However, there is not available in the market an integrated apparatus which is capable of therapeutically stimulating a patient automatically in response to information supplied from an oxygen or $CO_2$ measuring instruments so as to stimulate a patient to breathe more effectively when there is evidence that the patient's blood $CO_2$ level is high or $O_2$ is low compared to normal levels. There is therefore a need for an apparatus and method which can be used for reliably providing automatic stimulation of mammals in response to hypoxemic or hypercapnic conditions preceding true apnea by sensing the blood oxygen saturation level and/or $CO_2$ level in the blood of the patient.

In general, it is an object of the present invention to provide an apparatus and method for automatic stimulation of mammals in response to blood gas analysis.

Another object of the invention is to provide an apparatus and method which can be utilized for automatically and reliably stimulating a patient when an hypoxemic or hypercapnic condition occurs.

Another object of the invention is to provide an apparatus and method which before stimulating the patient introduces a pre-stimulus delay to prevent false positive detection.

Another object of the invention is to provide an apparatus and method in which a stimulus is provided which provides sufficient time for the patient's blood gas level to return to a predetermined level before a second stimulation is given to the patient.

Another object of the invention is to provide an apparatus and method in which another patient characteristic such as respiration effectiveness is sensed and analyzed prior to stimulation of the patient.

Another object of the invention is to provide an apparatus and method of the above character in which the stimulation given to the patient can be programmed to be at a level which is in direct response to the level of the patient characteristic being measured.

Another object of the invention is to provide an apparatus and method of the above character which can be programmed to increase the intensity of the stimulus given to the patient in response to the time which has elapsed after a predetermined patient threshold is reached.

Another object of the invention is to provide an apparatus and method of the above character in which different types of stimuli may be provided to stimulate the patient to cause the patient to resume normal breathing.

Another object of the invention is to provide an apparatus and method of the above character in which local and remote alarm capabilities are provided.

Another object of the invention is to provide an apparatus and method of the above character which is small and compact and has relatively low power consumption requirements.

Another object of the invention is to provide an apparatus and method of the above character which is capable of recording the blood gas levels, breathing rate, etc. being monitored.

Another object of the invention is to provide an apparatus and method of the above character which records the stimuli which have been given to the patient during a predetermined period of time.

Another object of the invention is to provide an apparatus and method of the above character which can be used by sleep-apnea patients for nighttime use.

Another object of the invention is to provide an apparatus and method of the above character in which the apparatus can be in the form of a hand-held device.

Additional objects and features of the invention will appear from the following description in which the preferred embodiments are set forth in conjunction with the accompanying drawings.

FIG. 1 is a block diagram of an apparatus incorporating the present invention for automatic stimulation of mammals in response to blood gas analysis by peripheral nerve stimulation or alternatively by auditory stimulation.

FIG. 2 is a circuit diagram of the peripheral nerve stimulator which includes interface circuitry for interfacing with the computer.

FIG. 3 is a perspective view of a hand-held device showing an alternative embodiment of the invention which can be utilized for hypoxemia and apnea detection.

FIG. 4 is an isometric view of the hand-held device shown in FIG. 3 with certain parts of the case being broken away.

In general, the apparatus for automatic stimulation of a patient is comprised of means adapted to be coupled to the patient for measuring the saturation level of a gas (such as oxygen or $CO_2$) in the blood of the patient and providing an electrical signal representative of the measured saturation level or actual or absolute level of the gas in the blood. Computer means is provided for receiving the electrical signal and generating the control signal when the measured saturation level falls below a predetermined value. Peripheral nerve stimulation means is adapted to be coupled to the patient and is coupled to the computer means and provides a nerve stimulant to the patient when the control signal is received.

In the method for automatic stimulation of a patient, the steps of the method are comprised of measuring the saturation level of a gas in the blood of the patient and supplying an electrical signal representative of the measured saturation level, ascertaining when the measured saturation level falls below a predetermined level and generating a control signal, and stimulating the patient in response to the control signal.

A pre-stimulus delay can be provided to make it possible to ascertain whether certain requirements for stimulation have been met to eliminate false positive detection. In addition, an inter stimulus delay can be provided so that the saturation of the predetermined gas in the blood of the patient has an opportunity to return to normal prior to applying a second stimulation to the patient.

More in particular as shown in the drawings, the apparatus for automatic stimulation of a patient is shown in FIG. 1. The patient 11 which is shown in FIG. 1 is shown as a human being having a torso 12 with legs 13 and arms 14 with fingers 15 on the arms. It should be understood that the patient can be any form of any mammal such as horses, dogs, cats and the like which are in the form of warm-blooded vertebrates. In all such mammals, the blood has saturated gas therein which can be analyzed by appropriate instrumentation. In addition, such mammals have lungs which inhale atmospheric gas.

The apparatus which is adapted to be coupled to the patient 11 is comprised of a device 17 for measuring the saturation level of a gas in the blood of a patient. The device can be of any suitable type as, for example, a pulse oximeter such as a Model 505 Pulse Oximeter supplied by Novametrix Medical Systems Inc. of Wallingford, Conn. 06492. The pulse oximeter measures the percentage of oxygen saturation of arterial blood in the patient and the pulse rate of the patient. The oximeter 17 includes a sensor 18. The sensor 18 forms a part of the oximeter and can be in the form of a finger cuff as shown, or alternatively an ear clip and flexible sensors which are available for adult and neonatal patients.

The sensor 18 includes an opto-electronic device 19 which is shown schematically in FIG. 1 which includes an opto-transistor Q1 of a suitable type which has its emitter connected to ground and which has its collector connected to +V through a resistor R1. The base of the transistor Q1 is exposed to the light emitting diode D1 which emits light of a suitable wavelength when energized. The connectors between the finger cuff sensor 18 and the oximeter 17 are made through a cable 20.

The pulse oximeter can be programmed to provide high and low limits which can be continuously displayed and which can be retained in the memory provided in the device. The output of the oximeter 17 is supplied to an analog to digital converter 21 identified as A/D which converts the analog output from the oximeter 17 to a digital output which is supplied to a crystal controlled microprocessor controller 22. The microprocessor 22 is provided with a program in its memory which samples the information from the analog to digital converter 21 and compares it to preprogrammed thresholds or levels for the parameter being measured by the device 17. If for example, the device 17 is an oximeter and is measuring the oxygen saturation level in the blood, the microprocessor which can be provided with one or more saturation levels which could be utilized to initiate stimulation with the present apparatus. The program of the microprocessor 22 includes certain appropriate delays which can be used to ensure that stimulation is required for the patient and to prevent false positive detection. By way of example, oxygen saturation in the blood is often monitored to give a reliable indication of whether an apnea condition (a temporary stopping of breathing) is, in fact, occurring to prevent the detection of false positive. False positive can occur when there is a rapid change in the oxygen saturation in the blood as, which for example, could be introduced by motion artifacts of the patient rather than actual physiological changes in the patient. The condition or the program of the microprocessor could be provided with a pre-stimulus delay which requires that before stimulation is applied to the patient as hereinafter described, that the apnea condition persist for a period of time greater than the pre-stimulus delay to again avoid false positive detection and stimulation. In addition, an inter stimulus delay can be provided which allows sufficient time for the patient's oxygen level to return to normal prior to stimulating the patient a second time. In addition to further improve the reliability of the apparatus hereinbefore described, an additional characteristic of the patient can be monitored, as for example, the respiration rate of the patient.

The microprocessor controller 22 is connected to a RAM 23 in the form of a static memory chip that is controlled by the microprocessor 22 to store data as, for example, the blood oxygen saturation level of the patient, the time and date and the type of stimulation imparted to the patient.

This information can be stored in the RAM 23 for later review by the attending physician. The RAM 23 permits downloading of data from the RAM 23 to other apparatus which may be used to read the information stored in the RAM 23.

When the predetermined parameters have been met in the microprocessor 22, the microprocessor supplies a control signal to a peripheral nerve stimulator 26. The peripheral nerve stimulator 26 is connected to conventional EKG pads 29 which are in electrical contact with the patient at spaced apart points as, for example, on one of the arms 13 of the patient 11 through conventional EKG leads 27 and 28. The leads 27 and 28 are isolated from the other components of the peripheral nerve stimulator 26 by an isolation transformer 31 which serves to prevent flow of ground currents into the patient.

The microprocessor 22 also supplies information to a display drive 36 that drives an LCD display 37 which can be utilized for displaying desired information from the microprocessor 22. A keyboard 38 of a conventional type is provided which is connected to the microprocessor 22 for inputting information into the microprocessor. The keyboard 38 can be of a conventional type and can be utilized with various keys 39 as, for example, on and off keys, programming keys, alarm enabling or disabling keys and the like.

A battery 41 is provided for supplying DC power as indicated by the +V output to the various components of the apparatus as indicated. Serial communication ports or lines 42 and 43 are provided which are connected to the microprocessor controller 22 which permits programming of the microprocessor controller 22 with the appropriate thresholds for stimulation and detection.

A low voltage detection circuit 51 is provided for ascertaining when the battery 41 should be replaced. It is comprised of a comparator 52 which has a reference voltage 53 connected thereto and a resistive network consisting of interconnected resistors R2 and R3. Resistor R2 is connected to ground and resistor R3 is connected to +V of the battery 41. When a low voltage condition is detected on the battery, a signal is generated which is supplied to the microprocessor 22 to give an appropriate warning on the LCD display 37.

An alarm circuit 61 is provided which is connected to the microprocessor controller 22 for providing a remote and/or local alarm to alert medical personnel of a condition which may require intervention. Such an alarm circuit can be of a conventional type. For example, it can be as simple as a transistor Q2 driving a loudspeaker 62 to provide with an audible tone.

It should be appreciated that in addition to, or in place of the oximeter 17 other types of sensing devices can be used. For example, in vivo blood gas monitoring can be used as well as end tidal $CO_2$ monitors which monitor the exhaled respiratory gases of the patient as well as transcutaneous membrane devices measuring carbon dioxide and oxygen. All of these devices can have their outputs fed to A/D convertor 21 that is utilized to supply information to the microprocessor controller to operate the peripheral nerve stimulator.

It also should be appreciated that in place of the stimulator 26 other types of stimulators other than electrical stimulators can be used. For example, stimulators of an auditory nature or vibratory nature which have variations in amplitude and frequency can be utilized. Also a mechanical stimulator can be used, for example, to provide joint movement and stimulation.

FIG. 1 in addition to showing a peripheral nerve stimulator 26 also shows an auditory stimulator 63 which is believed in certain cases may be as effective and for some human beings more effective than a nerve stimulator 26 and particularly for human beings coming out of anesthesia. It is believed that this increased efficacy is achieved because it is believed that the auditory system in at least some humans tends to recover much more rapidly from anesthesia than other senses such as touch, heat, pain or visual sensations. In order to make the auditory stimulator 63 most effective, a voice very familiar to the person undergoing the general anesthesia as for example the spouse of a patient or the mother of a patient is recorded in the form of a very simple phrase as for example "Wake up, Johnny.". Such a phrase or other appropriate calls to the patient can be recorded by the use of recording means 64. The recording means 64 as shown in FIG. 1 consists of a microphone 65 for receiving the human voice to convert the sound waves to electrical waves which are amplified by an amplifier 66 and supplied to a continuously variable slope delta modulator (CVSD) 67 or any other analog to digital conversion means utilizing data compression. The information from the CVSD 67 is supplied to the microprocessor 22 and to the RAM 23 which serves to store the phrase or message therein in digital form. As hereinbefore explained, when the predetermined parameters have been met in the microprocessor 22, the microprocessor in addition or alternatively supplies a control signal to the auditory stimulator 63. This causes the phrase stored in the ram 23 to be supplied to a digital to analog converter 68 which converts the voice stored in digital form to analog form. The analog information is supplied through an amplifier 69 to a loud speaker 70 to thereby play the recorded phrase into the ears of the patient. Normally, a patient hearing his own name will respond much more readily than to random or white noise, as for example, from the loudspeaker 62 in the alarm 61.

A more detailed circuit diagram of the electronic interface provided as a part of the peripheral nerve stimulator 26 is shown in FIG. 2.

As shown therein, the output from the microprocessor controller 22 which can be in the form of a computer is connected to a parallel port connector 71 which is connected by leads 72 to an opto-isolator 73 which is operated from a separate DC power supply which is connected to a conventional AC plug 76. The battery 77 which is provided as a part of the circuitry in FIG. 2 can be the same type as the battery 41 shown in FIG. 1 providing a suitable voltage, as for example, 9 volts through an on/off switch 78. As shown, the opto-isolator 73 is connected to the 9 volt voltage provided by the battery 77 and is provided with 9 output lines 81–89, four of which lines 81–84 are used for controlling stimulation current levels through electronic switches 51–54. Line 81 provides a current control of 2.5 milliamperes, line 82 —5.0 milliamperes, line 83 —7.5 milliamperes and line 84 13 10 milliamperes to provide four current levels that can be utilized for stimulating the patient.

The other three lines 85, 86 and 87 are connected through resistors R1, R2 and R3 to three sets of interconnected transistors Q1, and Q2, Q3 and Q4 and Q5 and Q6 in which transistors Q1, Q3 and Q5 are NPN transistors and transistors Q2, Q4 and Q6 are PNP transistors. The conductors 85, 86 and 87 are connected to the bases of the transistors Q1, Q3 and Q5. The bases are also connected to ground through resistors R7, R8 and R9. The emitters of transistors Q1, Q3 and Q5 are connected to ground and the collectors are connected through resistors R4, R5 and R6 to the bases of transistors Q2, Q4 and Q6 through resistors R4, R5 and R6. The emitters of the PNP transistors Q2, Q4 and Q6 are connected to the +9 V voltage from the battery 77. The collectors are connected to the pulse generator 91. The collector for transistor Q2 is connected through a resistor R10 and a diode D3. The three sets of transistors control three different frequencies f1, f2 and f3 which by way of example can be 25, 50 and 100 hertz respectively supplied from the pulse generator 91. The NPN and PNP transistors are in series for each frequency control because the polarity of the signal coming from the computer requires an inversion of the signal. The pulse generator 91 supplies a pulse train 92 of the type shown in FIG. 2 which is supplied on conductors 93 and 94 to an appropriate pulse shaping network 96 of the type well known to those skilled in the art and to a pulse transformer 97. The pulse transformer is provided with an adjustable potentiometer tap 98 which is connected to a simulation lead 99.

The base resistors R7, R8 and R9 are connected to the bases of the transistors Q1, Q3 and Q5 and to ground and serve to keep the transistors Q1, Q3 and Q5 turned off so that stimulation is turned off when the connector 71 is not connected to the computer or the computer is not turned on.

The additional line 88 coming from the opto-isolator 73 is connected through a base resistor R11 to an NPN transistor Q7 that is connected through a resistor R12 to a light emitting diode D1 that is connected to the +V supply provided by the battery 77.

The line 89 from the opto-isolator 73 is connected to a gate 101 of a suitable type such as CMOS gate which is always powered on. The input of the gate 101 is connected through a resistor R13 to ground. The output of the gate 101 is connected through a resistor R14 to the base of a transistor Q8 that has its collector connected to ground through a capacitor C1 and which has its emitter connected to +V. The collector of the transistor Q8 provides a suitable ,output voltage such as 9 volts DC. The input of the gate 101 which is connected to the output of the opto-isolator 73 makes it possible for the computer to control the gate 101 by pulling the line 89 high which can occur just prior to authorizing stimulation to the patient as hereinafter described. As soon as the input of the gate 101 goes high, the output goes low because the gate 101 is an inverting gate. This turns on the transistor Q8 whose emitter is connected to the +V and whose collector then supplies +9 volts to the remainder of the circuitry with the exception of the opto-isolator which must be powered continuously to allow the computer to communicate with the gate 101. Since the gate 101 is a low power device, it makes it possible to greatly reduce power consumption and therefore makes possible an extended battery life.

The lines 81, 82, 83 and 84 are connected to solid state switches S1, S2, S3 and S4 which can be of a suitable type such as CD 4066 supplied by RCA. The control lines of the switches are connected to ground through resistors R15, R16, R17 and R18 as shown in FIG. 2. The resistors R15 through R18 are utilized to keep the switches S1, S2, S3 and S4 turned off in the event the connector 71 is not connected to a computer or the computer is turned off. One side of each of the switches is connected to ground. The other sides of the switches are connected to adjustable potentiometers R19, R20, R21 and R22 and are connected in turn through resistors R23, 24, 25 and 26 to the negative input of an operational amplifier 101 by a line 102 and to the positive input of an operational amplifier 104 by a line 105 connected through a resistor R27. The output of the operational amplifier 102 is also connected to the positive input of the operational amplifier 104.

The output of the operational amplifier 104 is supplied through a base resistor R28 to a high voltage transistor Q9 which has its emitter connected to the negative terminal of the operational amplifier 104 and has it collector connected to the negative patient stimulation lead 106. The emitter of the transistor Q9 is also connected to ground through a resistor R29.

The positive terminal of the operational amplifier 102 is connected to the +9 voltage from transistor Q8 through a resistor R30 and is connected to ground through a Zener diode D2 and is also connected to ground through a capacitor C2.

In operation, the first operational amplifier 102 creates a reference voltage on its output which is adjustable depending upon which of the switches S1 through S4 is closed. The operational amplifier 102 is provided with a very stable reference voltage from the diode D2. It multiplies its reference voltage by a factor which is determined by a ratio of the resistor R27 and the resistor in each of the four legs connected to the switches S1, S2, S3 and S4 depending upon which switch is closed. In this manner, a voltage is created which is equivalent to the 2.5, 5.0, 7.5 and 10 milliampere currents through the patient leads 99 and 106.

The second operational amplifier 104 controls the patient stimulation current by taking the voltage supplied by the first operational amplifier 102 and supplies its output to the transistor Q9 and thereby controls the collector current in accordance with the reference voltage supplied on its positive input. Thus if the switch S1 is closed, the operational amplifier 104 would control the transistor Q9 so that voltage across R29 would be equal to the voltage at the output of the operational amplifier. Since the current flowing through R29 is approximately equal to the collector current of Q9, the collector current of Q9 is proportional to the output voltage of operational amplifier 102. It can be seen that the circuitry is such so that a programmed current is provided to the patient regardless of the impedance between the leads 102. This makes it unnecessary to adjust the apparatus for each patient. A predetermined selected current level flows into the patient regardless of the impedance of the patient under the control of the microprocessor.

When the on/off switch 78 is closed, the CMOS gate is powered up or turned on. This is not undesirable since the current required is less than 100 nanoamperes. The input to the gate 101 is connected to the output line 89 from the opto-isolator 73. When it is desired to stimulate a patient, the computer will cause the voltage on the line 89 to go high as indicated in the waveform 121. Since the CMOS gate 101 is an inverting gate, the output from the gate 101 goes low as shown by waveform 122 and turns on the transistor Q8 whose emitter is connected to the +B. The collector of the transistor Q8 then supplies a +9 volts to the remainder of the circuitry with the exception of the opto-isolator which must be kept alive to permit the computer to communicate with the CMOS gate 101.

Operation of the apparatus in performing the method for automatic stimulation of a patient 11 can now be briefly explained as follows. By way of example, let it be assumed that a human patient 11 under heavy sedation and pain control is located in an open floor ward in a hospital with very little nursing care and requires a lot of pain medicine. In such a situation, the patient 11 is an ideal one for use of the apparatus and method of the present invention. The patient 11 is connected to the apparatus in the method shown in FIG. 1 in which the finger cuff sensor 18 is placed on the finger of the patient 11 and the pads 29 are mounted on two separate locations on the other arm of the patient. Alternatively, a $CO_2$ measuring device could be attached to the nose-mouth complex of the patient.

Let it be assumed that the patient 11 has received pain medicine in sufficient quantity to cause a decrease in the respiration rate of the patient to cause an impending apnea condition to occur in the patient. The apparatus of the present invention senses this condition through use of the oximeter 17 which ascertains when the oxygen saturation level in the blood of the patient is below an acceptable level and causes the microprocessor 22 to provide an electrical stimulus to the patient in accordance with the previously selected current value.

When the pulse oximeter has detected a hypoxemic, pre-apneic condition in a patient, the apparatus causes the patient to be stimulated and thereby causes the patient to start breathing more effectively again. As the oxygen level increases as the patient starts breathing more effectively again, the pulse oximeter senses this and supplies signals through the A/D converter to the microprocessor 22 to turn off the stimulator 22. The microprocessor 22 includes the capabilities for providing additional stimulations or stimuli to the patient 11 in the event it becomes necessary. If the hypoxemic condition of the patient worsens rather than improving, the microprocessor 22 increases the amplitude and frequency of the stimuli and decreases the intervals of time between stimuli. The stimulations will be terminated by the microprocessor as soon as the patient starts to breathe more effectively. This condition is sensed by the oximeter 17 which senses the increased oxygen saturation level in the blood of the patient.

The importance of such an apparatus and method for use as a lifesaving device is appropriate in many locations, as for examples, anesthesia recovery rooms, ICU's on open floors in hospitals and in other medical situations. Even though attendants may be present, an attendant may not be able to act sufficiently quickly. The use of such apparatus is particularly desirable in such situations, particularly where life safety is involved.

It can be seen that the foregoing apparatus provides a computerized microprocessor integration of an oximeter and a peripheral nerve stimulator utilizing negative feedback.

Another embodiment of the invention is shown in FIGS. 3 and 4 in which the apparatus takes the form of a hand-held device 126. The device 126 has a cylindrical housing 127 which can have a suitable diameter as, for example, one inch and a length of 3½ inches.

Electronic circuitry is provided within the housing 127 and can take the form of integrated circuits as shown which include a miniature pulse oximeter, a peripheral nerve stimulator and the other electronics shown in FIG. 1 mounted on a PC board 131 mounted on the housing 127 in one compartment 132. The capabilities of miniaturizing such circuitry by providing custom integrated circuits is well known to those skilled in the art and is readily achievable.

Also included within the housing 27 is a battery 133 mounted in another compartment 134 in the housing 127 and separated from compartment 132 by a wall 136. The positive terminal of the battery 133 engages a contact 137 mounted on the wall 136 and connected to the circuitry on the PC board 131. The battery 133 is yieldably urged into engagement with the contact 137 by a spring 138 that also serves to make a negative contact with the battery 133. The spring 138 engages a contact (not shown) mounted in a removable insert of insulating material 139 mounted in the housing 127 and retained therein by a C-ring 141. A stop switch 142 is mounted in the end plate 139 and is utilized for stopping stimulation as hereinafter described.

An audio alarm is provided as a part of the electronic circuitry in the compartment 132 and includes a speaker 143 within the compartment 132 for providing an audible alarm. A connector 144 is provided in the compartment 132 and is connected to the electronics on the PC board 13. The connector 144 can be used for programming and/or interrogation.

The sensor for the hand-held device 26 can be of the type hereinbefore described as, for example, a finger cuff sensor 146 which is connected by a cable 147 to a terminal 148 mounted in an end plate 149 and which is connected to the circuitry in the housing 127.

Positive and negative contact members are carried by the housing 127 and are shown in the form of snap contacts 151 and 152 of a conventional type typically of the female type utilized in connection with EKG tests. The snap contacts 152 and 153 are connected electrically to the circuitry provided within the case 127 hereinbefore described.

Means is provided for retaining the hand-held device 26 in the palm of the hand of an appropriate type. For example, as shown it can consist of a two-piece Velcro band 156 which has its opposite ends secured to the case 127 and which is adapted to extend over the back side of the palm of the hand. The Velcro band 156 can be readily adjusted to fit different sizes of hands. The contacts 151 and 152 carried by the case 127 will engage the palm of the hand so that stimulation can be readily applied to a hand of a patient at two-spaced apart points when an apnea condition is sensed in the patient.

It should be appreciated that if additional assurance is required that electrical contact be made with the hand of the patient, male contacts, conventional EKG pads (not shown) of a type well known to those skilled in the art can be inserted into the female contacts 151 and 152 which can be secured to the palm of the hand in a manner well known to those skilled in the art.

If it is desired to have additional assurance that the handheld device will remain with the hand of the patient, a Velcro wrist band 161 can be provided which is adapted to fit over the wrist of the hand carrying the housing 127. The wrist band 161 can also be formed of Velcro straps which can be adjusted to fit the wrist of the wearer. If desired this wrist band 161 can be provided with positive and negative contacts (not shown) which can be utilized for stimulation of the patient at the wrist rather than stimulating the patient in the hand. Flexible tie strings 164 and 166 can be provided which are secured to opposite ends of the housing 127. In this way, the wrist band 161 can be utilized for stabilizing the position of the housing in the housing 127 in the hand. Also if desired, one of the strings 164 and 166 can carry conductors which are connected to the electronics in the housing 127 and to the contacts (not shown) so that stimulation can be provided at the wrist of the wearer rather than in the hand.

The hand-held device 126 is particularly useful for patients in hospitals. In addition it can be utilized in the home where patients are subject to sleep apnea. In such situations, the patient upon retiring can attach the device to his hand so that a stimulant can be given to the patient in his sleep in the event apnea occurs. As soon as the patient awakes, the patient can press the button 142 to stop further stimulation.

From the foregoing it can be seen that there is provided an apparatus and method for automatic stimulation of mammals in response to blood gas analysis. Although the apparatus and method has been described particularly for use with humans, it is readily apparent that the device can be utilized with other mammals, such as horses, cats, dogs and the like. With the apparatus and method automatic stimulation can be applied when an approaching hypoxemic, pre-apneic or true apnea condition is detected. The apparatus includes means for preventing false positive from stimulating the patient. The apparatus can be programmed to provide stimulations of a physical nature of increased amplitude and frequency where hypoxemic or hypercapnic conditions persist. Local and remote alarms can be provided.

What is claimed is:

1. A method for the automatic stimulation of a patient comprising measuring a saturation level of a predetermined gas in the blood of the patient and supplying an electrical signal representative of the measured saturation level, generating a control signal in response to the electrical signal when the measured saturation level falls below a predetermined value automatically stimulating the patient, by applying stimuli having a frequency and amplitude at intervals of time when a control signal is received, continuing sensing of the saturation level to ascertain when the measured saturation level continues to fall indicating a worsening condition of the patient and automatically increasing the frequency and amplitude of the stimuli and decreasing the intervals of time between stimuli in accordance with the worsening condition of the patient.

2. A method as in claim 1 wherein the stimuli include physical stimulations.

3. A method as in claim 2 further comprising the steps of providing progressive stimulation to the patient as long as the measured saturation level falls below a predetermined value.

4. A method as in claim 3 wherein the progressive stimulation is carried out by supplying DC pulses to the patient.

* * * * *